United States Patent [19]
Nicolaï et al.

[11] Patent Number: 5,686,460
[45] Date of Patent: Nov. 11, 1997

[54] CARBOCYCLIC DIARYLMETHYLENE DERIVATIVES, PROCESSES FOR THEIR PREPARATION AND THEIR USES IN THERAPEUTICS

[75] Inventors: Eric Nicolaï ; Michèle Launay, both of Rueil Malmaison; Dominique Potin, Aubergenville; Jean-Marie Teulon, La Celle Saint Cloud, all of France

[73] Assignee: Laboratoires UPSA, Agen, France

[21] Appl. No.: 723,449

[22] Filed: Oct. 7, 1996

[30] Foreign Application Priority Data

Aug. 1, 1996 [FR] France .................. 96 09742

[51] Int. Cl.$^6$ .................. A61K 31/44; A61K 31/18; A61K 31/10; C07D 213/61
[52] U.S. Cl. .................. 514/277; 514/345; 514/348; 514/349; 514/352; 514/464; 514/604; 514/709; 514/90; 546/296; 546/297; 546/303; 546/307; 546/345; 564/90; 568/34; 549/434; 549/445
[58] Field of Search .................. 546/345, 296, 546/297, 303, 307; 564/90; 568/34; 549/445, 434; 514/277, 464, 604, 709, 352, 345, 348, 349

[56] References Cited

FOREIGN PATENT DOCUMENTS 311899  4/1989  European Pat. Off. .

*Primary Examiner*—C. Warren Ivy
*Assistant Examiner*—Evelyn Huang
*Attorney, Agent, or Firm*—Aldo A. Algieri

[57] ABSTRACT

The present invention relates to the carbocyclic diarylmethylene derivatives of formula (I):

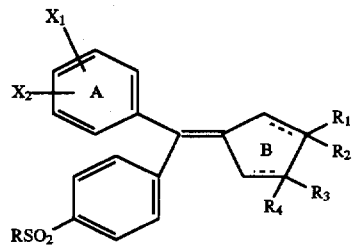

and to their use in therapeutics, especially as drugs with anti-inflammatory and analgesic properties.

17 Claims, No Drawings

CARBOCYCLIC DIARYLMETHYLENE DERIVATIVES, PROCESSES FOR THEIR PREPARATION AND THEIR USES IN THERAPEUTICS

The present invention relates to the carbocyclic diarylmethylene derivatives of general formula (I) as novel products.

One of the biotransformation pathways of arachidonic acid is the cyclo-oxygenase pathway, which makes it possible to transform arachidonic acid to PGG2 and then PGH2. Recent work on the cloning and sequencing of cyclooxygenase has revealed the presence of two isoenzymes, namely cyclooxygenase-1 (COX-1) and cyclooxygenase-2 (COX-2), in several species and particularly in man. The first is a constitutive enzyme which is expressed in the majority of tissues, while the second, which is expressed in a few tissues such as the brain, is inducible in the majority of tissues by numerous products, in particular by the cytokines and the mediators produced during the inflammatory reaction. Each enzyme has a different role and the inhibition of COX-1 or COX-2 will not have identical consequences. The inhibition of COX-1 will cause a decrease in the prostaglandins participating in homeostasis, which can give rise to side effects. The inhibition of COX-2 will cause a decrease in the prostaglandins produced in an inflammatory situation. Thus the selective inhibition of COX-2 makes it possible to obtain a well-tolerated anti-inflammatory.

The compounds of the invention make it possible to achieve this selective inhibition. The compounds in question consequently have a very valuable pharmacological profile insofar as they possess anti-inflammatory and analgesic properties while being remarkably well tolerated, especially in gastric terms. They will be particularly indicated for the treatment of inflammatory phenomena and for the treatment of pain.

An example of their use which may be mentioned is the treatment of arthritis, especially rheumatoid arthritis, spondylitis, gouty arthritis, osteoarthritis, juvenile arthritis, autoimmune diseases and lupus erythematosus. They will also be indicated for the treatment of bronchial asthma, dysmenorrhea, tendinitis, bursitis and dermatological inflammations such as psoriasis, eczema, burns and dermatitis. They can also be used for the treatment of gastrointestinal inflammations, Crohn's disease, gastritis and ulcerative colitis.

Their analgesic properties also enable them to be used for any pain symptoms, especially in the treatment of myalgia, articular pain or neuralgia, dental pain, herpes zoster and migraine, in the treatment of rheumatic complaints and pain of cancerous origin, and also as complementary treatments for infectious and febrile states.

The present invention further relates to the process for the preparation of said products and to their applications in therapeutics.

These carbocyclic diarylmethylene derivatives have general formula (I):

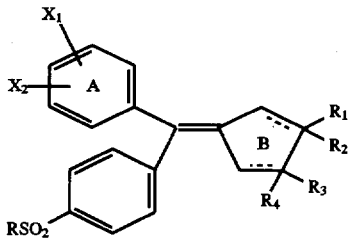

Formula (I)

in which:
the ring A is:
a phenyl ring or
a pyridyl ring;
the ring B is a ring containing five carbon atoms:
which is saturated, or
unsaturated, in which case $R_2$ and/or $R_4$ are absent in order to respect the valencies of the carbon atom;
$X_1$ and $X_2$ independently are:
the hydrogen atom,
a halogen atom,
a hydroxyl group,
a lower alkyl radical having 1 to 6 carbon atoms,
a trifluoromethyl radical,
a lower O-alkyl radical having 1 to 6 carbon atoms, or
a radical $NR_5R_6$,
or else $X_1$ and $X_2$ are a methylenedioxy group;
$R_1$, $R_2$, $R_3$ and $R_4$ independently are:
the hydrogen atom,
a halogen atom;
a lower alkyl radical having 1 to 6 carbon atoms, or
a lower haloalkyl radical having 1 to 6 carbon atoms,
or else $R_1R_2$ or $R_3R_4$ form, together with the carbon atom to which they are attached, a saturated hydrocarbon ring having from 3 to 6 carbon atoms;
$R_5$ and $R_6$ independently are:
a lower alkyl radical having 1 to 6 carbon atoms, or
the hydrogen atom; and
R is:
a lower alkyl radical having 1 to 6 carbon atoms,
a lower haloalkyl radical having 1 to 6 carbon atoms, or
a group $NH_2$.

In the description and the claims, lower alkyl is understood as meaning a linear or branched hydrocarbon chain having from 1 to 6 carbon atoms. A lower alkyl radical is for example a methyl, ethyl, propyl, isopropyl, butyl, isobutyl, tertbutyl, pentyl, isopentyl, hexyl or isohexyl radical.

Lower haloalkyl radical is understood as meaning an alkyl radical having 1 to 6 carbon atoms in which 1 to 7 hydrogen atoms have been substituted by 1 to 7 halogen atoms. A lower haloalkyl radical is for example a trifluoromethyl radical, a 2,2,2-trifluoroethyl radical, a pentafluoroethyl radical, a 2,2-difluoro-3,3,3-trifluoropropyl radical, a heptafluoropropyl radical or a chloromethyl or bromomethyl radical.

Halogen is understood as meaning a chlorine, bromine, iodine or fluorine atom.

Saturated hydrocarbon ring having from 3 to 6 carbon atoms is understood as meaning cyclopropane, cyclobutane, cyclopentane or cyclohexane.

In the cases where the above-mentioned derivatives of formula (I) have centers of asymmetry and/or exist in the form of cis or trans derivatives, the invention covers the racemates and the mixtures of cis and trans compounds, but also covers the optically active products, the cis derivatives and the trans derivatives taken independently. These pure products will be obtained by the methods known to those skilled in the art, in particular by chromatography, especially on chiral columns in the case of optical isomers.

Advantageously the derivatives according to the invention are the derivatives of formula (I) above in which:
the ring A is:
a phenyl ring or a pyridyl ring;

the ring B is a ring containing five carbon atoms which is:

saturated, or unsaturated, in which case $R_2$ and/or $R_4$ are absent in order to respect the valencies of the carbon atom;

$X_1$ and $X_2$ independently are:

the hydrogen atom, a halogen atom, a lower alkyl radical having 1 to 6 carbon atoms, a lower O-alkyl radical having 1 to 6 carbon atoms, or a radical $NR_5R_6$;

$R_1$, $R_2$, $R_3$ and $R_4$ independently are the hydrogen atom;

$R_5$ and $R_6$ independently are a lower alkyl radical having 1 to 6 carbon atoms; and R is:

a lower alkyl radical having 1 to 6 carbon atoms, or a group $NH_2$.

Within the framework of the present invention, it will be advantageous to use a compound of formula (I) in which at least one of the following conditions is satisfied:

the ring A is a phenyl ring or a pyridyl ring, the ring B is a cyclopentane or a cyclopentadiene, $X_1$ is a fluorine atom, a chlorine atom, a methyl radical, a methoxy radical or a dimethylamino radical, $X_2$ is a hydrogen atom or a fluorine atom, $R_1$, $R_2$, $R_3$ and $R_4$ independently are the hydrogen atom or $R_1$ and $R_3$ are the hydrogen atom and R2 and R4 are absent, and R is a methyl radical or a group $NH_2$.

The particularly preferred compounds of the invention are the following derivatives:

2-chloro-5-[(cyclopentylidene)(4-methylsulfonylphenyl)methyl]pyridine

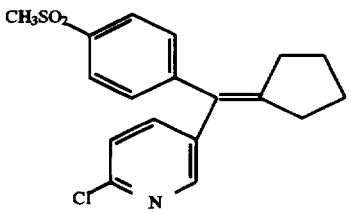

4-[(cyclopentylidene)(4-fluorophenyl)methyl]methylsulfonylbenzene

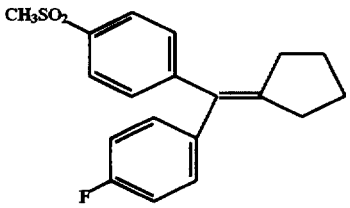

4-[(cyclopenta-2,4-dienylidene)(4-fluorophenyl)methyl]methylsulfonylbenzene

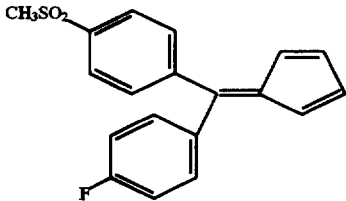

4-[(cyclopentylidene)(3-fluoro-4-methylphenyl)methyl]benzenesulfonamide

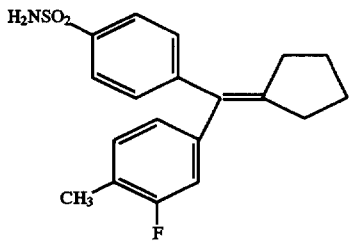

According to the invention, the compounds of formula (I) can be synthesized in the following manner:

A Friedel-Crafts reaction of the acid chloride of formula (II):

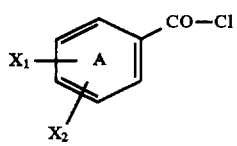

Formula (II)

in which A, $X_1$ and $X_2$ are as defined above, with thioanisole will give the benzophenone of formula (III):

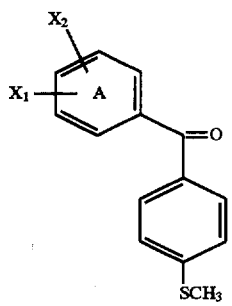

Formula (III)

in which A, $X_1$ and $X_2$ are as defined above.

Treatment of this benzophenone with an oxidizing agent, for example sodium perborate, $NaBO_3$, will give the derivative of formula (IV):

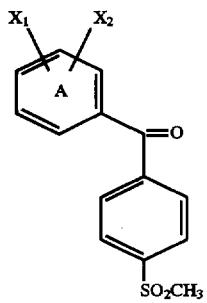

Formula (IV)

in which A, $X_1$ and $X_2$ are as defined above.

Reaction of a cyclopentanone, in the presence of lithium metal and titanium trichloride, $TiCl_3$, in dimethoxyethane, with the derivatives of formula (IV), according to the following reference:

M. M. CID, J. A. SEIJAS, M. C. VILLAVERDE and L. CASTEDO,

Tetrahedron 1988, vol. 44, no. 19, 6197 will give the compounds of formula (I) in which R is a methyl radical and B is a cyclopentane:

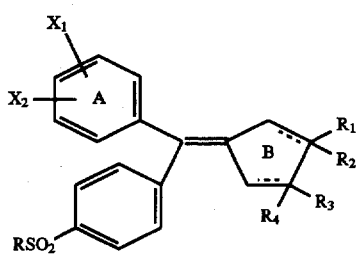

Formula (I)

Reaction of the lithium derivative of a cyclopentadiene, in tetrahydrofuran, with the derivatives of formula (IV), according to the following reference:

H. GILMAN and R. D. GORSICH, J. Org. Chem. 1985, 23, 550 will give the compounds of formula (I) in which R is a methyl radical, B is a cyclopentadiene and $R_2$ and $R_4$ are absent:

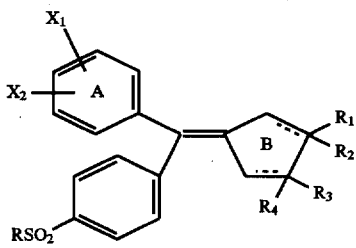

Formula (I)

These same methods will be used to prepare the compounds of formula (I) in which R is a lower alkyl other than methyl, the thioanisole being replaced with an alkylthiobenzene in the preparation of the benzophenone (III).

Another way of preparing the compounds of formula (I) consists in treating 4-fluorobenzonitrile with benzylmercaptan in dimethylformamide or 2-butanone, for example, in the presence of potassium carbonate, to give 4-benzyl-thiobenzonitrile according to the following equation:

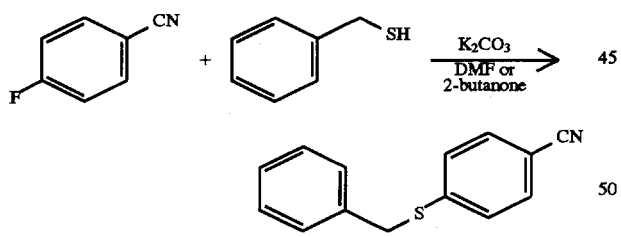

and then treating the latter with a compound of formula (V):

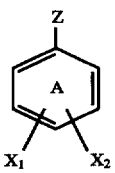

Formula (V)

in which $X_1$ and $X_2$ are as defined above and Z is MgBr when A is a phenyl and Li when A is a pyridine, to give the compounds of formula (VI):

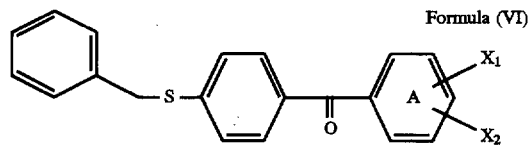

Formula (VI)

in which $X_1$, $X_2$ and A are as defined above.

Oxidation of the compounds of formula (VI) with chlorine, followed by treatment with dibenzylamine, will give the compounds of formula (VII):

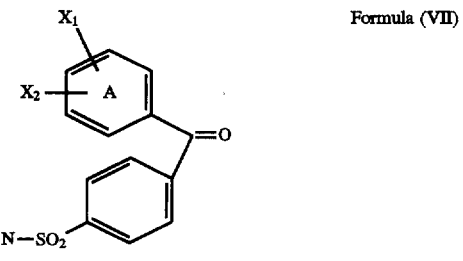

Formula (VII)

in which $X_1$, $X_2$ and A are as defined above and Ph is the phenyl ring.

Like the compounds of formula (IV), the benzophenones of formula (VII) may be treated with a cyclopentanone in the presence of lithium metal and titanium trichloride, or with the lithium derivative of a cyclopentadiene, according to the references cited above, to give the compounds of formula (VIII):

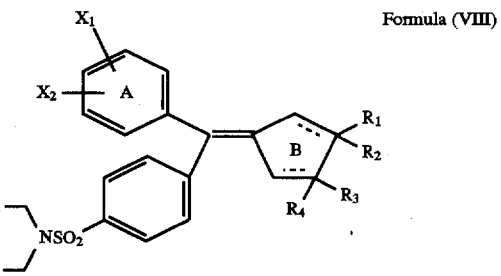

Formula (VIII)

in which A, $X_1$, $X_2$, $R_1$, $R_2$, $R_3$, $R_4$, B and Ph are as defined above.

Treatment of the compounds of formula (VIII) with methanesulfonic acid or with trifluoroacetic acid under reflux will give the compounds of formula (I) in which R is the group $NH_2$:

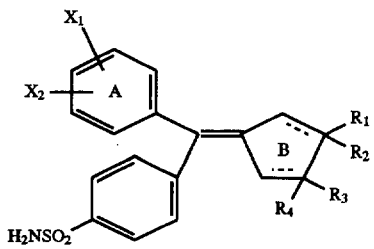

The compounds of formula (I) in which $R_1$, $R_2$, $R_3$, $R_4$, B and R are as defined above, A is a pyridine ring, $X_2$ is the hydrogen atom and $X_1$ is a group $NR_5R_6$, in which $R_5$ and $R_6$ are as defined above, can be synthesized by reacting an amine of the formula $HNR_5R_6$ with the corresponding derivatives of formula (I) in which $X_1$ is the chlorine or bromine atom, at a temperature between 80° and 200° C., in a solvent such as an alcohol or an aromatic solvent, for example toluene or xylene.

The compounds of formula (I) as defined above are cyclooxygenase-2 inhibitors and possess a very good anti-inflammatory and analgesic activity coupled with an excellent tolerance, particularly gastric tolerance.

These properties justify their application in therapeutics and the invention further relates, by way of drugs, to the products as defined by formula (I) above.

Thus the invention also covers a pharmaceutical composition characterised in that it comprises a pharmaceutically effective amount of at least one compound of formula (I) as defined above, optionally incorporated in a pharmaceutically acceptable excipient, vehicle or carrier.

These compositions can be administered by the buccal, rectal, parenteral, transdermal, ocular, nasal or auricular route.

These compositions can be solid or liquid and can be presented in the pharmaceutical forms commonly used in human medicine, for example simple or coated tablets, gelatin capsules, granules, suppositories, injectable preparations, transdermal systems, eye drops, aerosols and sprays, and ear drops. They are prepared by the customary methods. The active principle, which consists of a pharmaceutically effective amount of at least one compound of formula (I) as defined above, can be incorporated therein together with excipients normally employed in pharmaceutical compositions, such as talc, gum arabic, lactose, starch, magnesium stearate, polyvidone, cellulose derivatives, cocoa butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavorings and colors.

The invention also covers a pharmaceutical composition with anti-inflammatory and analgesic activity which can be used especially as a favorable treatment for inflammatory phenomena and pain, said composition being characterised in that it comprises a pharmaceutically effective amount of at least one compound of formula (I) above, optionally incorporated in a pharmaceutically acceptable excipient, vehicle or carrier. In one embodiment, a pharmaceutical composition with anti-inflammatory and analgesic activity is prepared which can be used especially as a favorable treatment for various inflammations and pain.

In one variant, a composition is formulated as gelatin capsules or tablets containing a dose of 1 mg to 1000 mg, or as injectable preparations containing a dose of 0.1 mg to 500 mg. It is also possible to use compositions formulated as suppositories, ointments, creams, gels, aerosol preparations, transdermal preparations or plasters.

The invention also covers a method of therapeutic treatment for mammals, wherein a therapeutically effective amount of at least one compound of formula (I) as defined above is administered to said mammal. In one variant of this method of treatment, the compound of formula (I), either by itself or in association with a pharmaceutically acceptable excipient, is formulated as gelatin capsules or tablets containing a dose of 1 mg to 1000 mg for oral administration, as injectable preparations containing a dose of 0.1 mg to 500 mg or as suppositories, ointments, creams, gels or aerosol preparations.

This method affords especially a favorable treatment for inflammatory phenomena and pain.

In human and animal therapeutics, the compounds of formula (I) can be administered, by themselves or in association with a physiologically acceptable excipient, in any form, in particular orally in the form of gelatin capsules or tablets, or parenterally in the form of injectable solutions. It is possible to envisage other forms of administration such as suppositories, ointments, creams, gels or aerosol preparations.

As will be clearly apparent from the pharmacological experiments given at the end of the description, the compounds according to the invention can be administered in human therapeutics, in the above-mentioned indications, orally in the form of tablets or gelatin capsules containing a dose of 1 mg to 1000 mg, or parenterally in the form of injectable preparations containing a dose of 0.1 mg to 500 mg, in one or more daily dosage units, for an adult with an average weight of 60 to 70 kg.

In animal therapeutics, the daily dose which can be used is between 0.1 mg and 100 mg per kg.

Further characteristics and advantages of the invention will be understood more clearly from the following few Examples, which in no way imply a limitation but are given by way of illustration.

Example 1: 4-Fluoro-4'-methylthiobenzophenone

Formula (III): A=phenyl, $X_1$=4-F, $X_2$=H 86.4 g of aluminum trichloride are added in portions, at a temperature between 0° C. and 5° C., to a solution of 70 g (0.564 mol) of thioanisole and 90.2 g (0.654 mol) of 4-fluorobenzoyl chloride in 500 ml of dichloromethane. When the addition has ended, the mixture is brought back to room temperature and then refluxed for 2 hours. After cooling, the reaction medium is poured into an ice/dilute hydrochloric acid mixture and the organic phase is separated and then dried over magnesium sulfate and evaporated under vacuum to give a residue, which crystallizes from isopropyl ether to give 118 g of 4-fluoro-4'-methylthiobenzophenone melting at 88° C.

Example 2: 4-Fluoro-4'-methylsulfonylbenzophenone

Formula (IV): A=phenyl, $X_1$=4-F, $X_2$=H 165 g of sodium perborate trihydrate are added in portions to a solution of 90 g (0.380 mol) of 4-fluoro-4'-methylthiobenzophenone, prepared in Example 1, in 800 ml of acetic acid, heated to 45° C. The mixture is subsequently stirred at 50° C. for 6 hours and then brought back to room temperature, and water is added. The precipitate obtained is filtered off and washed with water and then dissolved in dichloromethane. The resulting organic phase is dried over magnesium sulfate and evaporated under vacuum to give an oil, which crystallizes from isopropyl ether to give 93 g of 4-fluoro-4'-methylsulfonylbenzophenone melting at 136° C.

Example 3: 4-[(Cyclopentylidene)(4-fluorophenyl)methyl] methylsulfonylbenzene

Formula (I): A=phenyl, B=cyclopentane, $R_1=R_2=R_3=R_4$=H, R=$CH_3$, $X_1$=4-F, $X_2$=H 3.5 g (500 mmol) of lithium are added to a suspension of 25.4 g (165 mmol) of titanium trichloride in 300 ml of 1,2-dimethoxyethane. The mixture is refluxed for 2 hours and then cooled to room temperature. A solution of 7.5 g (27 mmol) of 4-fluoro-4'-methylsulfonylbenzophenone, prepared in Example 2, and 2.25 g (27 mmol) of cyclopentanone in 80 ml of 1,2-dimethoxyethane is added dropwise and the mixture is refluxed for 8 hours. After cooling, the mixture is treated with dilute hydrochloric acid solution and extracted with t-butyl methyl ether. The organic phase is dried over magnesium sulfate and evaporated under vacuum to give a residue, which is chromatographed on silica gel in dichloromethane. The resulting oil crystallizes from an isopropyl ether/pentane mixture to give 4 g of 4-[(cyclopentylidene)(4-fluorophenyl)methyl] methylsulfonylbenzene in the form of crystals melting at 84°–85° C.

Example 4: 2-Chloro-5-(4-methylthiobenzoyl)pyridine
Formula (III): A=3-pyridyl, $X_1$=6-Cl, $X_2$=H
Prepared by the procedure of Example 1.
Crystals melting at 145° C.

Example 5: 2-Chloro-5-(4-methylsulfonylbenzoyl)pyridine
Formula (IV): A=3-pyridyl, $X_1$=6-Cl, $X_2$=H A solution of 34.6 g of 2-chloro-5-(4-methylthiobenzoyl) pyridine, prepared in Example 4, and 42 g of sodium perborate trihydrate in 250 ml of acetic acid is heated for 4 hours at 45° C. The crystals formed are filtered off hot, washed with water and dried to give 32.6 g of 2-chloro-5-(4-methylsulfonylbenzoyl)pyridine in the form of crystals melting at 170° C.

Example 6: 2-Chloro-5-[(cyclopentylidene)(4-methylsulfonylphenyl) methyl]-pyridine
Formula (I): A=3-pyridyl, B=cyclopentane, $R_1$=$R_2$=$R_3$=$R_4$=H, R=$CH_3$, $X_1$=6-Cl, $X_2$=H Prepared by the procedure of Example 3 from the derivative of Example 5. Purified by chromatography on silica gel in an isopropyl ether/acetone mixture (95/5).

Crystals melting at 86°–88° C.

Example 7: 4-(Benzylthio)benzonitrile

A mixture of 37.2 g (300 mmol) of benzylmercaptan, 36.3 g (300 mmol) of 4-fluorobenzonitrile and 42 g of potassium carbonate in 700 ml of 2-butanone is refluxed for 7 hours. The solvent is evaporated off under vacuum and the residue is taken up with water and petroleum ether. The crystals formed are filtered off and washed with water and then with petroleum ether to give 46 g of 4-(benzylthio)benzonitrile in the form of crystals melting at 85° C.

Example 8: 3-Fluoro-4-methyl-4'-benzylthiobenzophenone
Formula (VI): A=phenyl, $X_1$=3-F, $X_2$=4-$CH_3$ A solution of 95 g (500 mmol) of 4-bromo-2-fluorotoluene in 200 ml of anhydrous ethyl ether is added dropwise to a suspension of 12.2 g (500 mmol) of magnesium turnings covered with anhydrous ethyl ether. When the addition has ended, the mixture is stirred for 30 minutes at room temperature and a solution of 50 g of 4-(benzylthio)benzonitrile in 200 ml of anhydrous tetrahydrofuran is then added dropwise. The ethyl ether is distilled and the mixture is refluxed for 6 hours. After cooling, the mixture is run dropwise into 600 ml of 6N hydrochloric acid solution and the resulting solution is refluxed for 6 hours. After the addition of isopropyl ether, the crystals formed are filtered off and washed with ethanol and then with ethyl ether to give 55.4 g of 3-fluoro-4-methyl-4'-benzylthiobenzophenone in the form of crystals melting at 122° C.

Example 9: N,N-Dibenzyl-4-[3-fluoro-4-methylbenzoyl]benzene sulfonamide
Formula (VII): A=phenyl, $X_1$=3-F, $X_2$=4-$CH_3$ Chlorine is bubbled up to the saturation point (50 g in 1 hour 30 minutes) into a solution of 55.4 g (165 mmol) of 3-fluoro-4-methyl-4'-benzylthiobenzophenone, prepared in Example 8, in 300 ml of acetic acid and 6 ml of water, cooled with an ice bath. The mixture is subsequently stirred at room temperature for 10 hours and then poured into iced water. The crystals formed are filtered off to give 53.7 g of a white solid melting at 90° C. The solid is dissolved in 200 ml of 1,2-dichloroethane, and 81 g of N,N-dibenzylamine are added. The mixture is refluxed for 1 hour and then cooled to room temperature. After the addition of dilute hydrochloric acid and isopropanol, the crystals formed are filtered off and the organic phase is separated, washed with water, dried over magnesium sulfate and evaporated to dryness under vacuum. The residue crystallizes from an ethyl ether/ethanol mixture to give 53 g of N,N-dibenzyl-4-[3-fluoro-4-methylbenzoyl]benzenesulfonamide in the form of crystals melting at 132° C.

Example 10: N,N-Dibenzyl-4-[(cyclopentylidene)(3-fluoro-4-methylphenyl)-methyl]benzenesulfonamide
Formula (VIII): A=phenyl, B=cyclopentane, $R_1$=$R_2$=$R_3$=$R_4$=H, R=N($CH_2$Ph)$_2$, $X_1$=3-F, $X_2$=4-$CH_3$ Prepared by the procedure of Example 3 from the derivative of Example 9. Purified by chromatography on silica gel in toluene.

Crystals melting at 105° C.

Example 11: 4-[(Cyclopentylidene) (3-fluoro-4-methylphenyl)methyl]benzene-sulfonamide
Formula (I): A=phenyl, B=cyclopentane, $R_1$=$R_2$=$R_3$=$R_4$=H, R=$NH_2$, $X_1$=3-F, $X_2$=4-$CH_3$ A solution of 6.5 g of N,N-dibenzyl-4-[(cyclopentylidene)(3-fluoro-4-methylphenyl)methyl]benzenesulfonamide, prepared in Example 10, in ml of trifluoroacetic acid is heated for 10 hours at 60° C. The mixture is poured into iced water and extracted with dichloromethane. The organic phase is washed with sodium bicarbonate solution, dried over magnesium sulfate and evaporated under vacuum. The residue is chromatographed on silica gel in a dichloromethane/acetone mixture (95/5) to give 3 g of 4-[(cyclopentylidene)(3-fluoro-4-methylphenyl)methyl]benzenesulfonamide in the form of a semicrystalline oil.

Example 12: 4-[(Cyclopenta-2,4-dienylidene)(4-fluorophenyl)methyl]methyl-sulfonylbenzene
Formula (I): A=phenyl, B=cyclopentadiene, $R_1$=$R_3$=H, R=$CH_3$, $X_1$=4-F, $X_2$=H, $R_2$ and $R_4$ are absent A solution of 3.7 g (50 mmol) of lithium cyclopentadienylide in 90 ml of anhydrous tetrahydrofuran is added to a solution of 11.1 g (40 mmol) of 4-fluoro-4'-methylsulfonylbenzophenone, prepared in Example 2, in 70 ml of anhydrous tetrahydrofuran, cooled to 10° C. The reaction medium is stirred for 2 hours at this temperature and then for 24 hours at room temperature. It is subsequently poured onto ice. After dilution with water, the mixture is extracted with t-butyl methyl ether. The organic phase is dried over magnesium sulfate and then concentrated in the cold. The residue obtained is chromatographed on silica gel in dichloromethane. The resulting oil crystallizes from a petroleum ether/t-butyl methyl ether mixture to give 3.6 g of 4-[(cyclopenta-2,4-dienylidene)(4-fluorophenyl)methyl]methylsulfonylbenzene in the form of orange crystals melting at 110° C.

Example 13: 2-(Dimethylamino)-5-[(cyclopentylidene)(4-methylsulfonylphenyl)methyl]pyridine
Formula (I): A=3-pyridyl, B=cyclopentane, $R_1$=$R_2$=$R_3$=$R_4$=H, R=$CH_3$, $X_1$=6-N($CH_3$)$_2$, $X_2$=H 4.5 g of 2-chloro-5-[(cyclopentylidene)(4-methylsulfonylphenyl)-methyl]pyridine, prepared in Example 6, and 50 ml of a 33% solution of dimethyl-amine in ethanol are placed in a 125 ml autoclave. The mixture is heated at 180° C. under pressure for 7 hours. After cooling, the solvent is evaporated off under vacuum and the residue is taken up with water and then extracted with dichloromethane. The organic phase is dried over magnesium sulfate and evaporated under vacuum. The resulting oil crystallizes from an ethyl ether/isopropyl ether mixture to give 2.8 g of 2-(dimethylamino)-5-[(cyclopentylidene)(4-methylsulfonylphenyl)methyl]pyridine in the form of crystals melting at 122°–123° C.

Example 14: 4-Methoxy-4'-methylthiobenzophenone
Formula (III): A=phenyl, $X_1$=4-$OCH_3$, $X_2$=H
Prepared by the procedure of Example 1.
Crystals melting at 130° C.

Example 15: 4-Methoxy-4'-methylsulfonylbenzophenone
Formula (IV): A=phenyl, $X_1$32 4-$OCH_3$, $X_2$=H
Prepared by the procedure of Example 2 from the derivative of Example 14.

Crystals melting at 203° C.

Example 16: 4-[(Cyclopenta-2,4-dienylidene)(4-methoxyphenyl)methyl]-methylsulfonylbenzene Formula (I): A=phenyl, B=cyclopentadiene, $R_1=R_3=H$, $R_2$ and $R_4$ are absent, $X_1=4\text{-}OCH_3$, $X_2=H$ Prepared by the procedure of Example 12 from the derivative of Example 15.

Crystals melting at 112°–113° C.

Example 17: 4-Chloro-4'-methylthiobenzophenone

Formula (III): A=phenyl, $X_1=4\text{-}Cl$, $X_2=H$

Prepared by the procedure of Example 1.

Crystals melting at 134° C.

Example 18: 4-Chloro-4'-methylsulfonylbenzophenone

Formula (IV): A=phenyl, $X_1=4\text{-}Cl$, $X_2=H$

Prepared by the procedure of Example 2 from the derivative of Example 17.

Crystals melting at 198° C.

Example 19: 4-[(Cyclopenta-2,4-dienylidene)(4-chlorophenyl)methyl]-methylsulfonylbenzene Formula (I): A=phenyl, B=cyclopentadiene, $R_1=R_3=H$, $R=CH_3$, $X_1=4\text{-}Cl$, $X_2=H$, $R_2$ and $R_4$ are absent Prepared by the procedure of Example 12 from the derivative of Example 18.

Crystals melting at 107°–108° C.

PHARMACOLOGY

The anti-inflammatory activity of the compounds of the Examples was evaluated by the carrageenin edema method and the analgesic activity was evaluated by the kaolin arthritis method.

Methods

Anti-inflammatory activity:

The anti-inflammatory activity is evaluated in the rat by the carrageenin edema test. The product is administered orally at a rate of 2.5 ml/100 g (n=6 animals per dose) 2 h 30 rain after oral hyperhydration (2.5 ml/100 g). One hour after administration of the product, the edema is induced by the plantar subcutaneous injection of 2% aqueous carrageenin solution. The percentage inhibition of the volume of the edema is calculated after 3 hours by measurement of the volume of the paw with a mercury plethysmograph.

Analgesic activity:

The analgesic activity is evaluated in the rat by the kaolin arthritis test. Thirty minutes after the intra-articular administration of 10% aqueous kaolin suspension, the product is administered orally at a rate of 1 ml/100 g (n=10 animals per dose). The percentage inhibition of the animal's pain response (grading of the gait) is calculated 5 h 30 rain after administration of the product.

| Example | Anti-inflammatory activity % inhibition (100 mg/kg) | Analgesic activity % inhibition (100 mg/kg) |
|---|---|---|
| 6 | 45.8 ± 9.8 | 55.0 ± 15.7 |

Inhibition of the COX-1 and COX-2 enzymatic activities

The molecule studied is preincubated for 10 minutes at 25° C. with 2 U of COX-1 (purified enzyme from ram seminal vesicles) or 1 U of COX-2 (purified enzyme from ewe placenta). Arachidonic acid (6 µM for COX-1, 4 µM for COX-2) is added to the reaction medium and incubation is carried out for 5 minutes at 25° C. When incubation has ended, the enzymatic reaction is stopped by the addition of 1N HCl and the PGE2 produced is determined by EIA.

The results are expressed as the percentage inhibition of the COX-1 and COX-2 enzymatic activities and correspond to mean±standard deviations of the average of 4 determinations.

| Example | % inhibition of the COX-2 activity | | % inhibition of the COX-1 activity |
|---|---|---|---|
| | $10^{-5}M$ | $10^{-7}M$ | $10^{-5}M$ |
| 3 | 66 ± 4 | 21 ± 4 | 0 ± 0 |
| 6 | 65 ± 2 | 18 ± 8 | 0 ± 0 |
| 12 | 57 ± 3 | — | — |

TOXICOLOGY

The first toxicology studies performed show that the products of the Examples do not induce a deleterious effect in the rat after the oral absorption of doses ranging up to 300 mg/kg.

What is claimed is:

1. A carbocyclic diarylmethylene compound of formula (I):

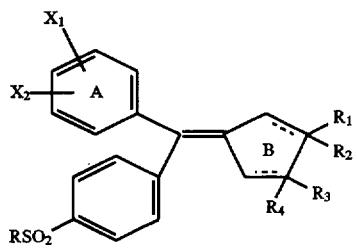

Formula (I)

in which:

the ring A is:
  a phenyl ring, or,
  a pyridyl ring;

the ring B is a ring containing five carbon atoms:
  which is saturated or
  unsaturated, in which case $R_2$ and/or $R_4$ are absent in order to respect the valencies of the carbon atom;

$X_1$ and $X_2$ independently are:
  the hydrogen atom,
  a halogen atom,
  a hydroxyl group,
  a lower alkyl radical having 1 to 6 carbon atoms,
  a trifluoromethyl radical,
  a lower O-alkyl radical having 1 to 6 carbon atoms, or
  a radical $NR_5R_6$,
or else $X_1$ and $X_2$ are a methylenedioxy group;

$R_1$, $R_2$, $R_3$ and $R_4$ independently are:
  the hydrogen atom,
  a halogen atom,
  a lower alkyl radical having 1 to 6 carbon atoms, or
  a lower haloalkyl radical having 1 to 6 carbon atoms, $R_5$ and $R_6$ independently are:
  a lower alkyl radical having 1 to 6 carbon atoms or
  the hydrogen atom; and R is:
  a lower alkyl radical having 1 to 6 carbon atoms,
  a lower haloalkyl radical having 1 to 6 carbon atoms, or
  a group $NH_2$.

2. A compound of formula (I) according to claim 1 in which:

the ring A is:
  a phenyl ring or
  a pyridyl ring;
the ring B is a ring containing five carbon atoms which is:
  saturated or
  unsaturated, in which case $R_2$ and/or $R_4$ are absent in order to respect the valencies of the carbon atom;
$X_1$ and $X_2$ independently are:
  the hydrogen atom,
  a halogen atom,
  a lower alkyl radical having 1 to 6 carbon atoms,
  a lower O-alkyl radical having 1 to 6 carbon atoms, or
  a radical $NR_5R_6$;
$R_1$, $R_2$, $R_3$ and $R_4$ independently are the hydrogen atom;
$R_5$ and $R_6$ independently are a lower alkyl radical having 1 to 6 carbon atoms; and
R is:
  a lower alkyl radical having 1 to 6 carbon atoms or
  a group $NH_2$.

3. A compound according to claim 1 wherein the ring B is selected from the group consisting of cyclopentane and cyclopentadiene.

4. A compound according to claim 1 wherein the ring A is selected from the group consisting of a phenyl ring and a pyridyl ring.

5. A compound according to claim 1 wherein $X_1$ is selected from the group consisting of a fluorine atom, a chlorine atom, a methyl radical, a methoxy radical and a dimethylamino radical.

6. A compound according to claim 1 wherein $X_2$ is selected from the group consisting of a hydrogen atom and a fluorine atom.

7. A compound according to claim 1 wherein $R_1$, $R_2$, $R_3$ and $R_4$ are the hydrogen atom.

8. A compound according to claim 1 wherein $R_1$ and $R_3$ are the hydrogen atom and $R_2$ and $R_4$ are absent.

9. A compound according to claim 1 wherein R is selected from the group consisting of a methyl radical and a group $NH_2$.

10. A compound according to claim 1 which is selected from the group consisting of:

2-chloro-5-[(cyclopentylidene)(4-methylsulfonylphenyl)methyl]pyridine

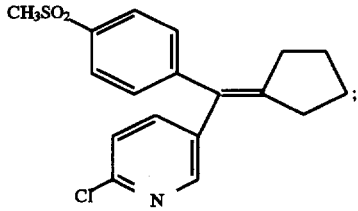

4-[(cyclopentylidene)(4-fluorophenyl)methyl]methylsulfonylbenzene

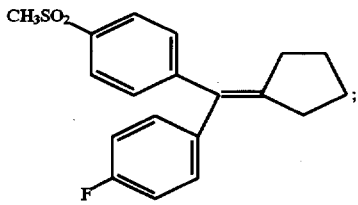

-continued
4-[(cyclopenta-2,4-dienylidene)(4-fluorophenyl)methyl]methylsulfonylbenzene

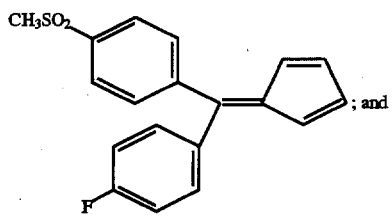

; and

4-[(cyclopentylidene)(3-fluoro-4-methylphenyl)methyl]benzenesulfonamide

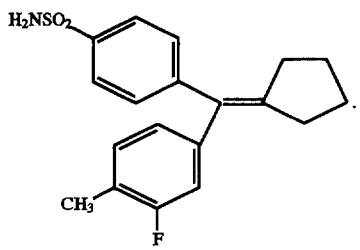

11. A process for the preparation of the compounds of formula (I) according to claim 1, which comprises reacting a benzophenone of the formula

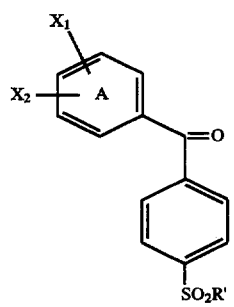

in which A, $X_1$ and $X_2$ are as defined in claim 1 and R' is selected from the group consisting of a lower alkyl having 1 to 6 carbon atoms and the group $N(CH_2Ph)_2$, Ph being a phenyl, with:

either a cyclopentanone, in the presence of lithium metal and titanium trichloride, in a solvent, or a lithium compound of a cyclopentadiene, the compounds in which R' is a group $N(CH_2Ph)_2$ then being treated with a reagent selected from the group of methanesulfonic acid and trifluoroacetic acid to give the compounds of formula (I) in which R is the group $NH_2$.

12. A pharmaceutical composition which comprises a pharmaceutically effective amount of a compound of formula (I) as defined in claim 1, incorporated in a pharmaceutically acceptable excipient, vehicle or carrier.

13. A pharmaceutical composition with anti-inflammatory and analgesic activity which contains a pharmaceutically effective amount of a compound of formula (I) as defined in claim 1, incorporated in a pharmaceutically acceptable excipient, vehicle or carrier.

14. A pharmaceutical composition according to claim 12 which is presented in the form of gelatin capsules or tablets containing a dose of 1 mg to 1000 mg.

15. A pharmaceutical composition according to claim 12 which is presented in the form of injectable preparations containing a dose of 0.1 mg to 500 mg.

16. A method for treating inflammation in a mammal which comprises administering an anti-inflammatory effective amount of a compound of formula I as defined in claim 1 to said mammal.

17. A method for treating pain in a mammal which comprises administering an effective amount of a compound of formula I as defined in claim 1 to said mammal.

* * * * *